United States Patent
Regimand et al.

(10) Patent No.: US 6,684,684 B2
(45) Date of Patent: Feb. 3, 2004

(54) SYSTEMS AND METHODS FOR DETERMINING THE POROSITY AND/OR EFFECTIVE AIR VOID CONTENT OF COMPACTED MATERIAL

(75) Inventors: Ali Regimand, Raleigh, NC (US); Lawrence James, Raleigh, NC (US)

(73) Assignee: InstroTek, Inc., Raleigh, NC (US)

( * ) Notice: Subject to any disclaimer, the term of this patent is extended or adjusted under 35 U.S.C. 154(b) by 132 days.

(21) Appl. No.: 10/061,409

(22) Filed: Feb. 1, 2002

(65) Prior Publication Data

US 2002/0162383 A1 Nov. 7, 2002

Related U.S. Application Data

(63) Continuation-in-part of application No. 09/976,530, filed on Oct. 11, 2001, and a continuation-in-part of application No. 09/580,792, filed on May 30, 2000.
(60) Provisional application No. 60/240,563, filed on Oct. 13, 2000.

(51) Int. Cl.[7] .................................................. G01N 15/08
(52) U.S. Cl. .......................................................... 73/38
(58) Field of Search ......................... 73/38, 32 R, 433, 73/437

(56) References Cited

U.S. PATENT DOCUMENTS

| 4,083,228 A | 4/1978 | Turner et al. ................. 73/32 R |
| 4,176,965 A | 12/1979 | Ito et al. ..................... 73/432 R |
| 5,606,126 A | 2/1997 | Glenville ....................... 73/433 |
| 5,760,293 A | 6/1998 | Orr et al. ..................... 73/32 R |
| 6,321,589 B1 | 11/2001 | Regimand .................... 73/32 R |

FOREIGN PATENT DOCUMENTS

| DE | 20024530 A | 8/1971 |
| EP | 0936451 A1 | 8/1999 |
| JP | 62-269040 | 11/1988 |
| JP | 10010032 A | 1/1998 |

OTHER PUBLICATIONS

Birello et al., "Advance in density measurements by means of an automatic hydrostatic weighing system of 100 g capacity," Measurement, vol. 7, No. 4, pp. 157–162 (Oct.–Dec. 1989).

Dept. of Defense, "Standard Test Method for Percent Air Voids in Compacted Dense and Open Bituminous Paving Mixtures," ASTM Standards, Designation: D 3203–94, p. 286–287 (Nov. 1994).

Dept. of Defense, "Standard Test Method for Bulk Specific Gravity and Density of Compacted Bituminous Mixtures Using Paraffin–Coated Specimens," ASTM Standards, Designation: D1188, pp. 118–120 (Oct. 1996).

(List continued on next page.)

*Primary Examiner*—Richard A. Moller
(74) *Attorney, Agent, or Firm*—Myers Bigel Sibley & Sajovec PA (57) ABSTRACT

Methods, systems, and computer program products determine the porosity or effective air void content of a compacted material sample of pavement or construction materials undergoing analysis corresponding to different measurements of field or lab formed material samples. The effective air void content represents a subset of the total air void content of the material sample.

58 Claims, 7 Drawing Sheets

OTHER PUBLICATIONS

Dept. of Defense, "Standard Test Method for Bulk Specific Gravity and Density of Compacted Bituminous Mixtures Using Coated Samples", ASTM Standards, Designation: D 1188–96, pp. 122–125 (Oct. 1996). Updated Version.

Dept. of Defense, "Standard Test Method for Theoretical Maximum Specific Gravity and Density of Bituminous Paving Mixtures," ASTM Standards, Designation: D2041, pp. 176–182 (Dec. 1995).

Dept. of Defense, "Standard Test Method for Theoretical Maximum Specific Gravity and Density of Bituminous Paving Mixtures," ASTM Standards, Designation: D 2041–00, p. 183–186 (Oct. 2000). Updated Version.

Dept. of Defense, "Standard Test Method for Bulk Specific Gravity and Density of Non–Absorptive Compacted Bituminous Mixtures," ASTM Standards, Designation: D2726, pp. 242–244 (Oct. 1996).

Dept. of Defense, "Standard Test Method for Bulk Specific Gravity and Density of Non–Absorptive Compacted Bituminous Mixtures," ASTM Standards, Designation: D 2726–00 p. 245–248 (Sep. 2000). Updated Version.

FM5–565, Florida Method of Test for Measurement of Water Permeability of Compacted Asphalt Paving Mixtures, Mar., 1999, p. 1–8.

Huang et al., Fundamentals of Permeability in Asphalt Mixtures, 1999, p. 479–495.

Stephens, "Bituminous Mix Density by Coated Specimen," Project No. 67–5, Connecticut Dept. of Transportation (Jan. 1973).

Wolf, B., "Application of hydrostatic weighing to density determination of tiny porous samples," Rev. Sci. Instrum, vol. 66 (3), pp. 2578–2581 (Mar. 1995).

SYSTEMS AND METHODS FOR DETERMINING THE POROSITY AND/OR EFFECTIVE AIR VOID CONTENT OF COMPACTED MATERIAL

RELATED APPLICATIONS

This application is a continuation-in part of U.S. application Ser. No. 09/580,792, filed May 30, 2000. This application is also a continuation-in part of U.S. application Ser. No. 09/976,530, filed Oct. 11, 2001, which claims the benefit of priority from U.S. Provisional Application Ser. No. 60/240,563 filed Oct. 13, 2000. The contents of these documents are hereby incorporated by reference as if recited in full herein.

FIELD OF THE INVENTION

This invention is related to methods and systems used to evaluate air void contents or characteristics of compacted materials used in the construction of roads, foundations, and other structures.

BACKGROUND OF THE INVENTION

In recent years, design and use of open graded mixtures for the formation of paved roads have gained popularity. The term "open-graded mixtures" describes selections of mixed size compositions that can include various amounts of fine, medium, and coarse aggregates. When evaluating designs or performing quality control reviews or assessments of construction projects using open-graded mixtures, determining the air void content can be important because excessive air void content may be a precursor to the susceptibility of the roadway to have excessive water permeability that may, in turn, cause premature failure of the roadway. Thus, air void content is of concern in asphalt design and fabrication because it can provide an estimate of the mixtures' stability and/or durability.

Conventionally, design evaluation criteria for a particular mixture is generally based upon several parameters including % air void content. In the past, to assess the % air void content, the maximum specific gravity of a loose mixture and the bulk specific gravity of a compacted representative sample of HMA (hot mix asphalt) is determined. As is known to those of skill in the art, the maximum specific gravity is typically evaluated using a method described in ASTM D2041. In the asphalt mix design industry, the % air voids (ASTM D3203) can be calculated for compacted mixtures using the determined bulk specific gravity (Gmb) and the maximum specific gravity (Gmm) values of the sample.

This % air void determination method assumes that the size distribution and composition of the compacted mixture at the site is uniform and similar to the distribution and composition of the mixture used in the evaluation test (i.e., the ASTM D2041 test). Therefore, an average Gmm value is presumed to be a good representation of the maximum specific gravity of the mixture used in the design and, ultimately, the construction project itself.

Using an average Gmm value may be a valid approach when dealing with fine, dense graded mixtures of HMA. The fine dense graded mixture can generally be suitably uniformly distributed and thus the sample Gmm is generally representative of that in the field site. In addition, any potential inhomogeneous distribution of small or fine grade aggregates in a compacted sample of same should not significantly influence the resultant quantification of the air void content because, typically, small aggregate grain densities are sufficiently close so as to not cause significant variations in the determined bulk specific gravity of compacted fine dense mixtures.

In contrast, with coarse and/or open graded mixtures, uniformly splitting the sample can be problematic. It is noted that the term "coarse" is typically associated with aggregates retained on a 2.36 mm (No. 8) or larger sieve. In addition, it is oftentimes difficult to control the application of the open-grade mixture so as to obtain a substantially uniform distribution of the aggregate mixture in the field at the construction site when forming the roadway. Unfortunately, with coarse and/or open-grade mixtures, variation of large aggregate grains can significantly impact the bulk specific gravity (i.e., the Gmm and the Gmb values) of the sample. (See ASTM D2726 and D1188 for bulk specific gravity (Gmb) and ASTM D2041 for maximum specific gravity (Gmm), the contents of which are hereby incorporated by reference as if recited in full herein).

In view of the foregoing, there remains a need to provide air void content evaluation methods of open-graded and/or fine and/or coarse aggregate mixtures that can provide useful information about the potential life or durability of the resultant paved highway or roadway.

SUMMARY OF THE INVENTION

Embodiments of the present invention provide systems, methods, computer program products, and devices that can determine the porosity and/or effective air void content ("EAV") of an open grade mixture comprising coarse or fine aggregates and/or combinations thereof. As described herein, the terms "EAV" and % porosity are used interchangeably as the same measure of the same parameter (porosity). In certain embodiments, the sample comprises compacted bituminous or asphalt material mixtures and the measurement is used to provide a measure or indicator of the permeability, stability and/or durability of a roadway formed from the mixture composition.

The EAV parameter determination can be carried out so as to selectively assess that portion of the voids in the sample that are accessible to water or other environmental liquids and/or fluids during service and to substantially disregard that portion of the voids that is not accessible to liquids and/or fluids (such as water) during service. That is, in service, generally stated, the air voids of particular interest are those that are accessible to fluid entry because it is these voids that can impact the durability of the construction project and/or that may indicate a propensity for excessive water permeability. The air voids that are not accessible to fluid entry (such as water and air) are less important to asphalt designers, but by obtaining the data for the EAV parameter, it is possible to calculate this inaccessible fraction of air voids by utilizing the measurement of % air voids which indicates the total amount of voids (both accessible and inaccessible). The EAV evaluation can be used to evaluate proposed designs of desired compacted samples including those employing open-grade mixtures. The EAV evaluation can also be used to perform quality control review of completed portions of paved roadways and similar construction projects to assure that certain standards have been met.

The EAV parameter can be represented as the percentage of water permeable voids in a compacted mixture. The EAV parameter can be calculated using a bulk specific gravity and an apparent maximum gravity of any desired compacted sample. In certain embodiments, the EAV measurement or evaluation can be directly performed and does not require the use of a Gmm value or a previously determined Gmm value that may not be representative of the gradation of a randomly selected compacted sample. The EAV parameter can be used as a direct indicator of mixture durability and/or stability and can strongly correlate to mixture permeability and/or segregation.

In certain embodiments, the evaluation can be carried out relatively swiftly, typically in under about 10 minutes (such as in about 7 minutes).

In certain embodiments, statistical variations in the EAV value(s) can be monitored and used to provide process control parameters during construction to assess the material composite mixture segregation. Alternatively or additionally, if the EAV value(s) is smaller than the % air void value, stripping potential may be identified as this comparison can indicate water absorption into the aggregates. It is also possible to determine the packing potential or % voids between aggregates by using the EAV value and % absorption of the aggregates.

Certain embodiments of the invention are directed to methods of determining the effective air void content of a compacted material sample. The method includes the steps of: (a) encasing a compacted material sample in a conformable sealant material (having a known or predetermined weight); (b) evacuating the encased material sample; (c) sealing the encased material specimen to provide a vacuum-sealed encased material sample; (d) obtaining the weight of the encased vacuum-sealed material sample in air; (e) immersing the vacuum-sealed encased material sample in a liquid displacement bath; (f) obtaining the weight of the sealant sample in the liquid bath; (g) introducing an opening into the sealant material of the encased material specimen while the material specimen and sealant material are held immersed in the liquid bath to allow liquid to enter the sealant material and contact the material sample; (h) obtaining the weight of the encased material sample during the immersing step after the introducing step; and (i) determining the porosity or effective air void content parameter value of the material sample based on the obtaining steps.

In particular embodiments, the method can include the step of calculating both the density of the vacuum sealed encased compacted material sample ($\rho_1$) and the density of the vacuum sealed sample after opening the seal under liquid ($\rho_2$). The determining step can also be carried out so as to include the step of calculating the effective air void content parameter value (EAV) using the mathematical equation:

$$EAV = \left(\frac{\rho 2 - \rho 1}{\rho 2}\right) \times 100.$$

Knowing EAV, the inaccessible air void content (percentage) can be calculated by the mathematical equation:

Inaccessible air voids=% air voids−EAV.

Other embodiments of the present invention are directed to alternative methods for determining the effective air void content of a compacted material sample. The methods can include: (a) determining the bulk specific gravity of the material sample ($\rho_1$); (b) drying a compacted material sample; (c) obtaining a dry weight of the material sample; (d) positioning the material sample in a rigid sealable container of known volume; (e) obtaining a first weight of the material sample and container under ambient pressure conditions; (f) evacuating the container to introduce a vacuum onto the material sample held therein; (g) introducing a known quantity of liquid into the container in a quantity sufficient to cover the material sample; (h) releasing the vacuum in the container with the material sample held immersed in the liquid; (i) obtaining the weight of the material sample in the open container in the liquid after the releasing step; j) calculating the maximum apparent density ($\rho_2$); and (k) determining the effective air void content of the compacted material sample undergoing analysis based on the obtained weights.

The bulk specific gravity of step (a) can be determined in any suitable manner. For example, using a sealing method as described in U.S. Pat. No. 6,321,589 (the contents of which are hereby incorporated by reference as if recited in full herein), using the method described in ASTM D1188, or using a dimensional evaluation methodology (mass/volume) as is known to those of skill in the art.

Still other embodiments of the present invention are directed to computer program products for determining the porosity and/or effective air void content of a compacted material sample undergoing analysis. The computer program product includes: (a) a computer readable storage medium having computer readable program code embodied in said medium, said computer-readable program code comprising: (b) computer readable program code for accepting input corresponding to a weight measurement of a vacuum sealed compacted material sample held encased in a sealant material; (c) computer readable program code for accepting input corresponding to a weight measurement of the encased material sample as it is held under liquid with the vacuum seal destroyed; (d) computer program code defining predetermined mathematical relationships for determining the effective air void content of the compacted material sample; and (e) computer readable program code for calculating the effective air void content of the compacted material sample undergoing analysis based on the weight measurements and the pre-determined mathematical relationships.

In certain embodiments, the program can also include computer readable program code for calculating both the density of the vacuum sealed encased compacted material sample ($\rho_1$) and the density of the vacuum sealed sample after opening the seal under liquid ($\rho_2$). In addition, the computer readable program code for calculating porosity or effective air void content can include the same mathematical equation noted above.

The effective air void content parameter is calculated and determined so as to be a measure of a subset of the air voids in the material sample. That is, the effective air void parameter corresponds to air voids in the compacted material that are accessible to liquids during service and substantially excludes or disregards air voids in the compacted material sample that are inaccessible to liquid during service.

However, by knowing EAV and % air voids (the % air voids can be evaluated using suitable methods such as that described in ASTM D3203), the percentage of inaccessible air voids can be calculated if desired.

The above summary is not intended to limit the scope of the invention as other apparatus, fixtures, operations, and computer programs can also be used to carry out the methods of the present invention.

The foregoing and other objects and aspects of the present invention are explained in detail in the specification set forth below.

BRIEF DESCRIPTION OF THE DRAWINGS

FIGS. 4A–4D are front schematic views of a series of operations that can be used to determine the effective air void content parameter value of a compacted material sample according to embodiments of the present invention.

DESCRIPTION OF EMBODIMENTS OF THE INVENTION

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. Layers may be exaggerated for clarity. In the figures, broken lines, where used, indicate the associated operation or feature is optional.

Generally stated, embodiments of the present invention are directed to determining the porosity, % porosity, and/or effective air void content parameter value of a material sample. For asphalt applications, air voids in the compacted asphalt pavement appear in the mix as small pockets of air between the asphalt coated aggregate particles. Thus, for pavement quality, air voids in the mixture is an important consideration or parameter. Generally, designers design the mixture to a particular air void percentage by adjusting the aggregate blend and/or the asphalt content. However, as the proportion of coarse aggregates in the mixture increases, the air void that are connected (termed interconnected voids), may increase, allowing water to penetrate into the mixture. The present method for determination of % air void generally only evaluates the total air voids in the mixture and cannot distinguish between the voids that are interconnected, and, thus, permeable to water, and those that are substantially impermeable to water. Providing data that distinguishes between these two types of void content may allow designers to adjust the mixture design for improved performance.

In addition, in certain situations, it can be important to know the porosity of the mixture if the mixture is designed to be a drainage layer, such as pervious concrete mixes and open-graded friction asphalt courses. These mixes are specifically designed to allow water or liquid to drain through the construction site. When the porosity of the mixes is unknown or unreliable, the performance of the subgrade and/or the durability of the pavements may be disadvantageously impacted.

Figure 1A:
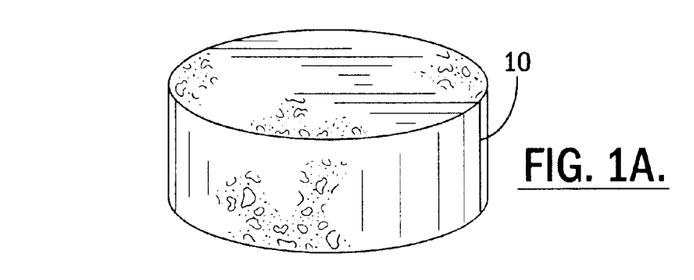
FIG. 1A is a perspective view of a compacted material sample selected for evaluation according to embodiments of the present invention.

Turning now to the figures, FIG. 1A illustrates a material sample 10. The material sample 10 for analysis can be selected such that it is representative of the material mixture. The material sample can be cored from the pavement section or can be compacted in the laboratory during design or quality control evaluation. The material sample 10 may include, fine or coarse aggregates, or combinations of fine and coarse aggregates (and may also include dust or mineral filler). As such, the material sample may be formed from a conglomerate of and/or contain a plurality of different aggregate composition types.

Embodiments of the present invention can be used to evaluate material samples comprising both fine and coarse aggregate mixtures. As noted above, the term "coarse aggregate" is typically applied to mineral and/or synthetic aggregate material that is retained on a 2.36 mm (No. 8) sieve. The term "fine aggregate" applies to material passing through the 2.36 mm (No. 8) sieve. Mineral filler or fine aggregate (including "very fine" aggregate) is applied to material of which at least 70% passes through a 75 $\mu$m (No. 200) sieve.

Asphalt and concrete pavements and/or asphalt and concrete specifications typically require that the aggregate particles are within a certain range of sizes and that each size is present in a certain proportion. The aggregate mixture may include aggregates of different shapes as well as aggregates of different material types. For example, many asphalt and/or concrete mixtures contain both angular and rounded aggregate particles. The coarse aggregate particles can be a crushed stone or gravel and the fine aggregate can be a natural sand (round particles) or stone screenings.

The present invention is suitable for evaluating compacted material samples. In particular embodiments, the compacted material sample can comprise asphalt-coated aggregates that are sufficiently compacted so as to retain a desired shape during evaluation. For example, the compacted material sample can be formed into a specimen shape such as a cubical (disk) or cylindrical shape. The compacted material samples can comprise open-graded mixtures or mixtures comprising fine and/or coarse aggregates. In particular embodiments, the compacted material samples are asphalt or (portland) cement (also known as PCC or portland cement concrete) coated compacted mixed size aggregates used to form pavement, roadways or other desired construction foundations.

The compacted materials can comprise synthetic and natural aggregate materials such as, but not limited to, sand, silica, glass, limestone, chat sand, LA #30, MM, bulk or loose asphalt, concrete cylinders or specimens, or other compacted materials or shaped or formed specimens. The materials or specimens can comprise non-absorptive (such as glass or metals) and/or absorptive materials (whether the material composition exhibits high, low, or intermediate absorption characteristics or porosity). Examples of some aggregates include blast furnace slag, synthetic and manufactured aggregates, and lightweight aggregates such as low-density materials (which may be used in concrete structures such as high-rise buildings).

The EAV and the "% porosity" are a measurement of the porosity of the sample. The EAV or % porosity parameter can provide an estimation of the permeability potential, asphalt mixture segregation, stripping potential, and, ultimately, pavement durability. Asphalt designers and practitioners can determine in a relatively short time period (such as in less than about seven-ten minutes) the EAV or % porosity parameter that may be a fundamental parameter in the assessment of the design and quality of the roadway that is purely dependent on the compacted sample under test. The results of this test do not require a previously determined maximum specific gravity test to be performed to establish the Gmm. This method can eliminate the need for Gmm measurements and the results of this test may be a superior method of indicating pavement distress and/or durability.

Figure 1B:
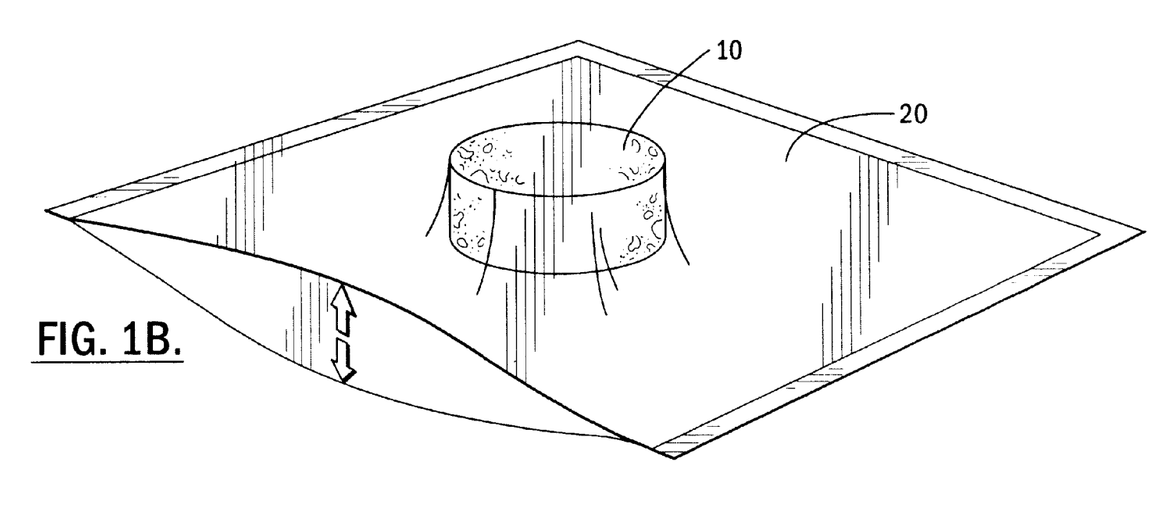
FIG. 1B is a perspective view of the compacted material shown in FIG. 1 inserted into a preformed sealable resilient bag according to embodiments of the present invention.

FIG. 1B illustrates that a compacted field or laboratory sample 10 is obtained and, in certain embodiments is then positioned inside a covering or casing 20. The sample 10 is then vacuum-sealed and encased inside a sealable casing or covering 20.

As shown, in particular embodiments, the covering or casing 20 is a preformed bag. The bag may be an elastomeric, plastic bag, elastomeric/foil lined bag, or other water resistant material bag. Suitable bags identified as Corelok® bags are available from InstroTek, Inc., located in Raleigh, N.C.

Alternately, other evacuated coverings can also be used including resilient elastomeric coverings that are formed over the sample in situ in the lab or testing facility. See e.g., Jack E. Stevens, *Bituminous Mix Density by Coated Specimen,* Project No. 67-5, Connecticut Dept. of Transportation, (Jan. 1973); Japanese Patent Publication No. 10010023A to Tousei Ltd; and Japanese Patent Publication No. 622690040 to Japan Steel Corporation. The contents of these references are hereby incorporated by reference as if recited in full herein. For ease of discussion, the figures and description will be directed to the preformed bag embodiment, but such description is not to be limiting to the scope of the invention. In particular embodiments, other container types can be used as long as they are configured to allow water to enter in after reaching an evacuated state with the material sample held therein as will be discussed further below.

Figure 2A:
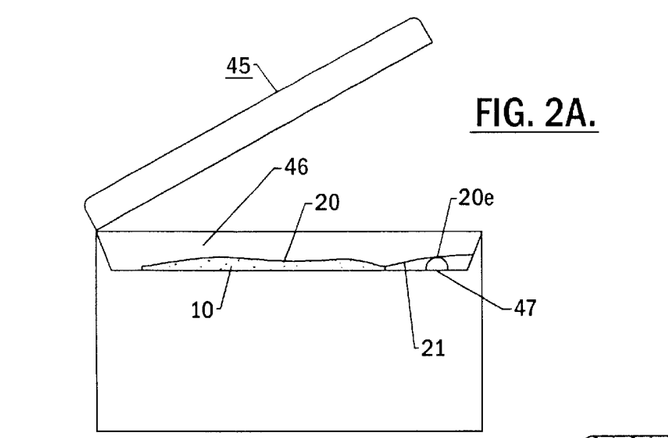
FIG. 2A is a side schematic view of a vacuum apparatus configured to seal the material sample in the bag shown in FIG. 1B according to embodiments of the present invention.
Figure 2B:
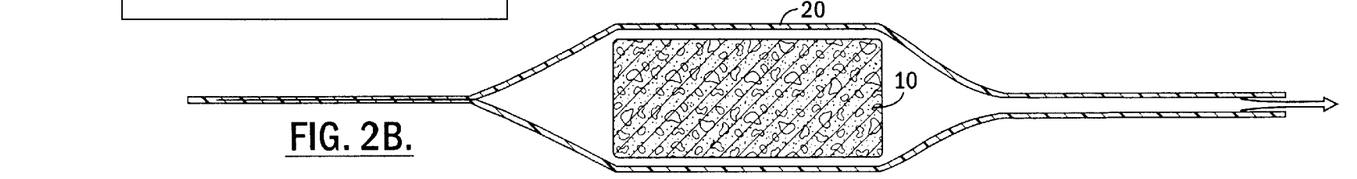
FIG. 2B is a side section view of the sample in the unsealed bag shown in FIG. 1B.
Figure 2C:
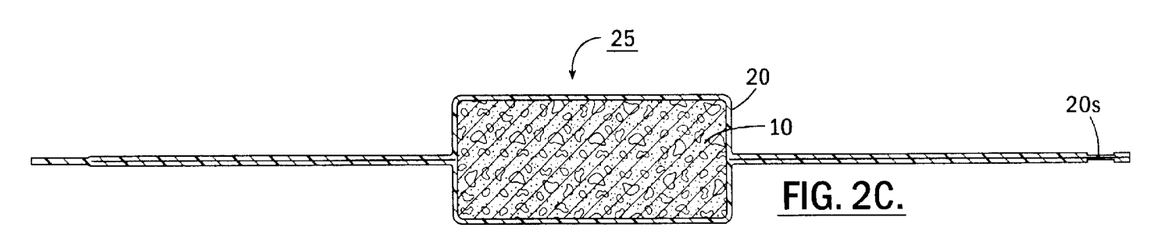
FIG. 2C is a side section view of the sample in a sealed evacuated bag according to embodiments of the present invention.

FIG. 2A illustrates that the sample 10 and covering 20 are evacuated and then sealed to form a vacuum-sealed encased specimen. FIG. 2A illustrates a suitable vacuum system 45 that includes a vacuum chamber 46 and a bag sealing means 47 such as a heating element or rod. FIG. 2B illustrates (by the direction of the arrow) that air is evacuated from the bag 20. FIG. 2C illustrates that the bag 20 is then sealed and collapsed to conform to and abut against the surface of the material sample 10 to provide a vacuum-sealed clad material sample 25. In operation, after evacuation and sealing, the vacuum chamber 46 can be configured to increase the pressure therein in a controlled manner to cause the bag to collapse against the enclosed perimeter surface of the sample. As shown, the bag 20 includes a sealed edge 20s. U.S. Pat. No. 6,321,589 and related U.S. patent application Ser. No. Ser. No. 09/580,792 provide additional description of suitable vacuum systems and operation, material sample evaluation methods, and preformed bags, the contents of which are hereby incorporated by reference as if recited in full herein. Suitable vacuum and evaluation systems are available from InstroTek, Inc., located in Raleigh, N.C.

Figure 3:
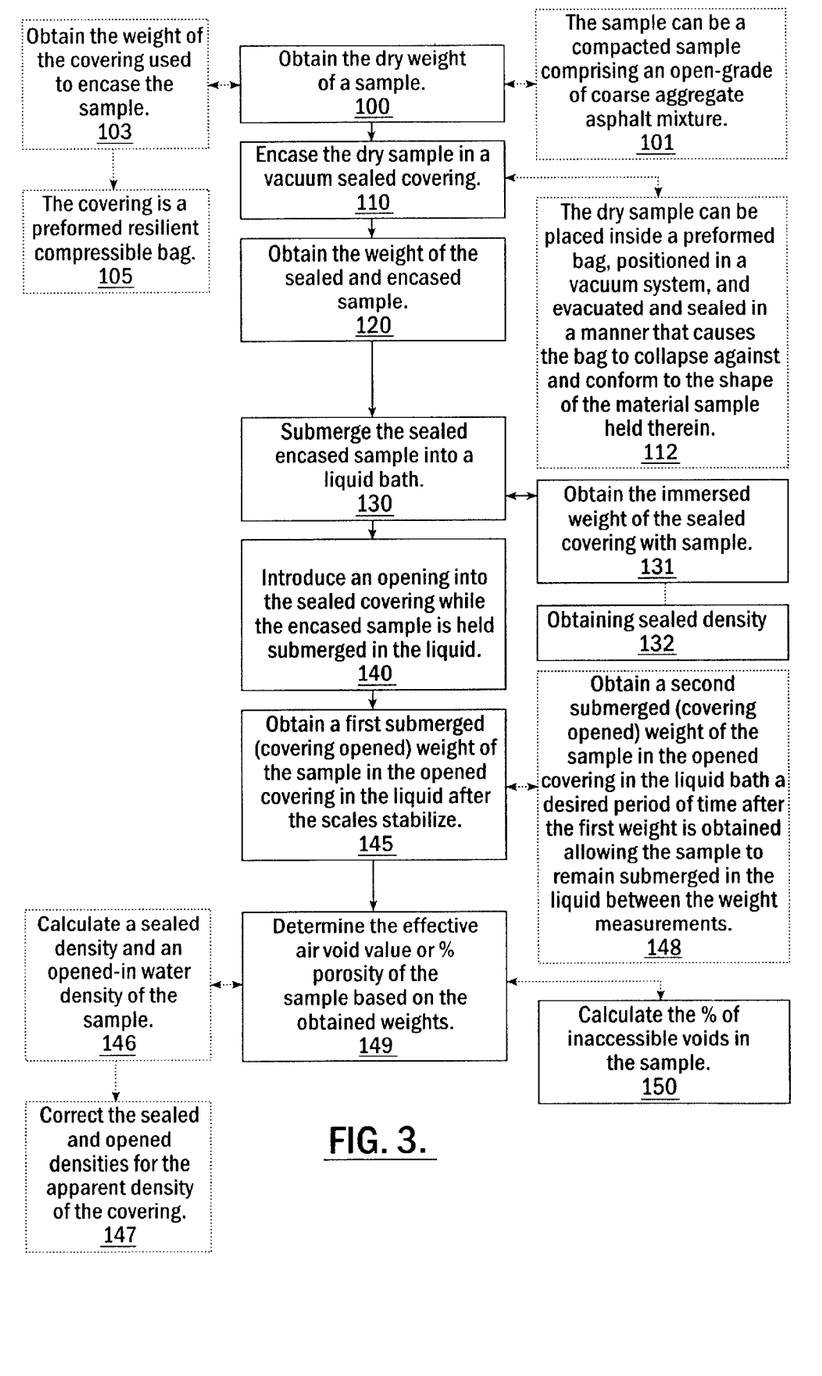
FIG. 3 is a block diagram of operations for determining the effective air void content of compacted samples such as compacted open grade, bituminous, or asphalt aggregate material samples, according to embodiments of the present invention.

FIG. 3 illustrates operations that may be performed to determine and/or evaluate the effective air void content parameter (EAV) according to embodiments of the present invention. The compacted sample 10 can be selected such that it is sized on the order of between about 100–5000 grams with a typical mass of about 4000 grains (usually for a 6 inch sample size). For composition mixtures comprising increased amounts of larger sized coarse aggregates, the sample portion size may approach 4000 grams or more. The sample 10 can be completely dried according to well-known procedures (such as oven drying). The dry weight of the compacted sample (non-encased) is obtained (block 100). The compacted material sample may comprise an open-graded or coarse aggregate asphalt mixture (block 101). The compacted sample can be a field or laboratory sample. The dried sample is encased in a vacuum-sealed covering (block 110).

The weight of the covering used to encase the sample can be obtained (block 103). The covering can be a preformed resilient compressible bag as described above (block 105). The apparent bag or covering density can be determined by an OEM or in the laboratory as described in U.S. Pat. No. 6,321,589 and related U.S. patent application Ser. No. Ser. No. 09/580,792. Thus, in certain embodiments, the dry sample can be placed inside a sealable preformed bag, positioned in a vacuum system, and then the bag sealed in a manner that causes it to collapse against and conform to the shape of the underlying or overlying material specimen held therein (block 112).

In any event, the weight of the vacuum-sealed encased sample is obtained (block 120). The vacuum-sealed encased sample is immersed or submerged into a liquid bath (block 130). The weight of the sealed covering with sample is obtained while it is immersed or submerged in the liquid (block 131). A sealed density of the specimen (with the vacuum intact) can be obtained or calculated (block 132). An opening is introduced into the sealed covering while the encased sample is held submerged or immersed in the liquid (block 140). A submerged or immersed weight (with the covering opened or unsealed) of the sample in the opened covering is obtained (block 145). The bag or covering can be opened by cutting, tearing, puncturing, or otherwise compromising the sealed integrity thereof. Thus, at least one opening is inserted into the bag or covering. In certain embodiments, after inserting the opening into the bag, the bag walls can be separated or pulled gently apart to allow water to enter therein, with care being taken to hold the sample and the bag completely under water.

The submerged weights (blocks 131, 145, and optionally 148) can be obtained by placing the encased sample on a suspended scale (FIG. 4C) or other weighing means. The submerged weight can be obtained after the scales are substantially stabilized, typically at about or within about 4 minutes (after opening the covering or bag such as via scissors or other implements or via a manual tear or the like, the liquid entering into the covering or bag can cause the weight to fluctuate). The effective air void parameter value can then be determined based on the obtained weights (block 149). The % or inaccessible voids in the sample can also be calculated in certain embodiments (block 150).

In certain embodiments, a second submerged weight (covering opened or unsealed) can be obtained a desired period of time after the first submerged weight (covering opened) while the sample and opened bag remain submerged or immersed in the liquid between the measurements (block 148). The second weight may be obtained after the opened bag and sample are allowed to sit in the bath for a period of 2–10 minutes, and typically about 4 minutes.

The sealed sample density and the opened-in liquid density of the encased sample can be calculated (block 146). These two calculated densities may be corrected or adjusted to account for the influence of the bag or covering, i.e., to account for the contribution of the apparent bag or covering density to the measurements and/or calculations (block 147).

To determine the EAV or effective air void parameter value, the dry sealed density, "$\rho_1$", can be calculated based on the submerged weight of the vacuum-sealed sample inside the bag or covering. A second density, "$\rho_2$", the density of the vacuum sealed sample after opening under liquid can be determined based on the submerged weight of the opened bag and sample. Since the sample is under complete vacuum prior to opening the bag in the liquid, $\rho_2$ will yield an apparent or maximum density of the compacted sample. The second density $\rho_2$ includes the volume due to accessible air voids. In this method, a standard equation can be used for calculation of the Effective Air Voids content:

$$EAV = \left(\frac{\rho 2 - \rho 1}{\rho 2}\right) \times 100 \quad \text{Equation (1)}$$

where
EAV=Effective Air Voids Content parameter;
$\rho_1$=the vacuum sealed density of a compacted material sample; and
$\rho_2$=the density of the vacuum-sealed sample after opening under water.

The densities can be calculated using the methodology and equations described in U.S. Pat. No. 6,321,589 and U.S. patent application Ser. No. 09/580,792, the contents of which are again incorporated by reference as if recited in full herein.

As noted above, in certain embodiments, a bag apparent density correction value (or other correction value for other containers as needed) and can be provided by an OEM or calculated as noted in co-pending and co-assigned U.S. patent application Ser. No. 09/580,792.

Figure 4A:
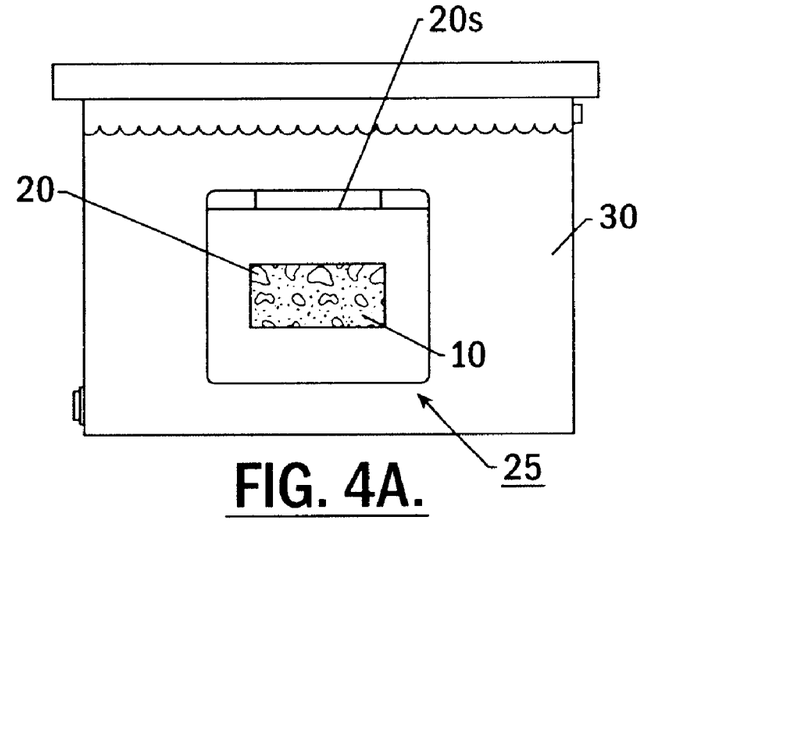
FIG. 4A Illustrates the evacuated sealed bag holding the material sample therein submerged in the liquid bath.
Figure 4B:
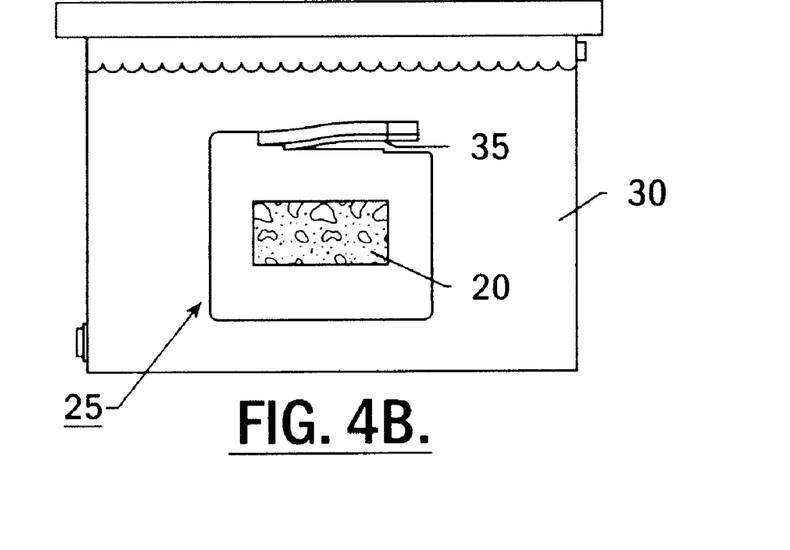
FIG. 4B illustrates an opening being introduced to the evacuated sealed bag holding the material sample as the bag and sample are held submerged under the liquid according to embodiments of the present invention.

FIG. 4A illustrates a vacuum-sealed encased compacted material sample 25 immersed into the liquid bath 30. FIG. 4B shows an opening 35 cut into the top portion of the bag 20. In certain embodiments, the opening(s) 35 can be sized to be about 1 inch–4 inches wide and/or long and can be introduced at an edge portion of the bag away from the material sample itself. Where an inner bag is used (not shown) for added puncture protection, care should also be taken to open both the inner and outer bags (while held immersed in the liquid) so that water or liquid can flow into both and contact the sample. In particular embodiments, it is possible to remove the bag or covering completely, and only measure the sample under water after a sealed sample weight (in air and/or submerged) is obtained.

Figure 4C:
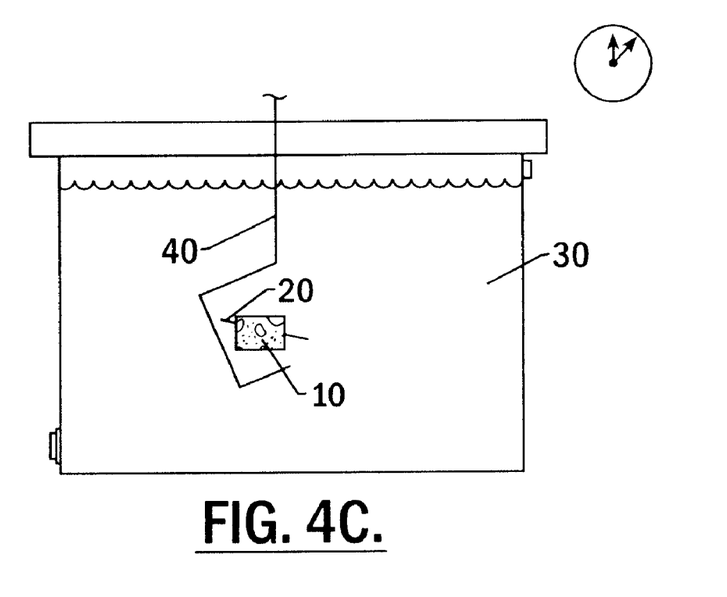
FIG. 4C illustrates that the weight of the sealed bag with sample is obtained while immersed in the liquid bath.

FIG. 4C illustrates that the submerged or immersed weight of the covered (sealed sample) is obtained. The encased sample 10 can be placed on the weighing basket 40 and the basket lowered into the bath 30 to submerge the encased sample 25 in the liquid bath 30. Alternatively, the encased sample 10 can be placed on the basket 40 or other weighing means after it is put in the bath 30.

Figure 4D:
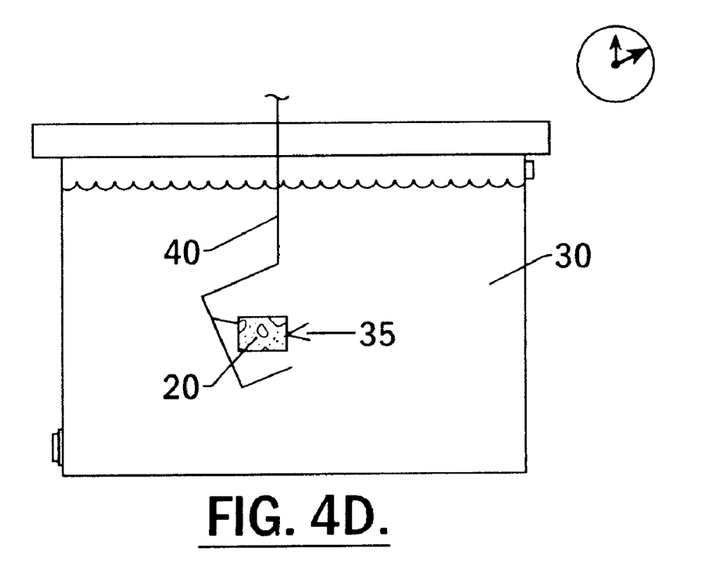
FIG. 4D illustrates that the weight of the opened bag and sample is obtained while immersed in the liquid bath.

As shown in FIG. 4D, to obtain the submerged weight, the opened bag 20 with sample 10 can also be placed on a weighing basket 40 remaining completely submerged. The bag 20 and sample 10 may be gently shaken or agitated to facilitate the removal of air bubbles adhering to the surface of the bag. As noted above, in particular embodiments, it is possible to remove the bag or covering completely, and only measure the sample under water after a sealed sample weight (in air and/or submerged) is obtained.

In any event, the weight of the sample 10 in the opened (previously evacuated and sealed) bag 20 is measured as the bag and sample are held under water. FIG. 4D illustrates that the opened bag sample can remain in the liquid for an additional time period after the first submerged weight is obtained and then a second submerged weight can be obtained. The opened bag may remain in the liquid for about 2–10 additional minutes (or longer as desired) and typically about 4 additional minutes from when the first weight is obtained.

Once EAV is determined, the percentage of inaccessible air voids can be calculated by subtracting the EAV value from the % Air Voids value (using conventional assessment means) to assess stripping potential, permeability, and/or other performance characteristics of the sample.

The measured weights can be input into a general purpose or special purpose processor, and computer program products and algorithms can calculate the EAV parameter value and other related values as desired in a relatively short analysis period (the entire procedure can be carried out in about 5–10 minutes not including the drying period).

Other embodiments of the present invention evaluate the EAV by evacuating a rigid container of a known volume that holds the material sample. Generally stated, in these embodiments, the EAV of the compacted sample can be calculated using weights of a rigid "calibrated" fixed volume container instead of using the opened submerged weight of the sample in an elastomeric or resilient covering or bag. In this process the maximum apparent density, $\rho_2$ can be measured. Before this process the bulk specific gravity (represented by the term ($\rho_1$) for this embodiment as it relates to equation (1)), is obtained using a suitable methodology (such as using a sealing method or a dimensional density calculation). The EAV in this embodiment can be calculated by using the established $\rho_1$ value and using a calibrated or known volume container that is evaluated at various process points such as (a) when empty; (b) when empty of liquid and holding the material sample; and (c) after evacuating the container when the material sample is held therein and a known amount of liquid is directed into the container to cover the sample (after being evacuated) while still held in the container at atmospheric conditions.

FIG. 7 illustrates examples of operations for carrying out the EAV or % porosity evaluation in this embodiment. The bulk specific gravity ($\rho_1$) is obtained (block 151). As shown, the weight of a compacted sample is obtained (block 152) as before. The sample can comprise an asphalt open-graded mixture (block 154). The sample is placed into a calibrated (known substantially constant volume) rigid container configured to be evacuated (block 155). The weight of the sample and container are obtained at atmospheric pressure (block 156). The container with the sample is evacuated (block 160). A known quantity of liquid is introduced into the calibrated or fixed volume container in an amount sufficient to cover the sample (block 165). In particular embodiments, the liquid is introduced into the calibrated container after the material is evacuated. In any event, the weight of the sample in the container with liquid is obtained after evacuation (block 166).

The pressure in the calibrated container can be returned to atmospheric pressure again before the weight is obtained. The scales should be allowed to stabilized before obtaining the weight.

The EAV of the material sample is determined based on the obtained weights (block 170). By comparing multiple sample values or a predetermined correlated relationship (that may be generated by using samples from the same construction site or project, but other correlation means can also be used), at least one of the durability, permeability, stripping potential, or mix segregation of the asphalt mixture or pavement formed therefrom can be assessed (block 172).

Figure 5:
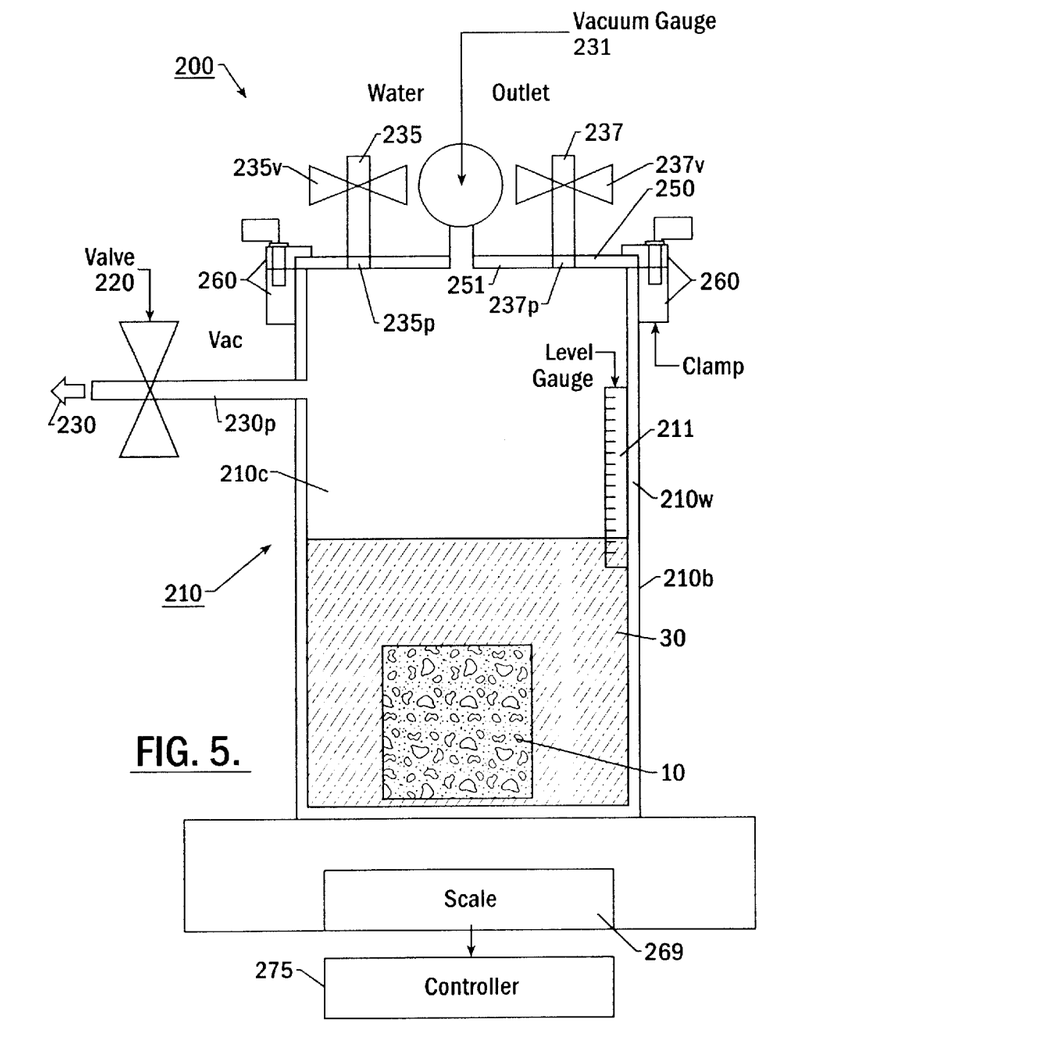
FIG. 5 is a schematic of a vacuum-sealable measurement system according to embodiments of the present invention.
Figure 6:
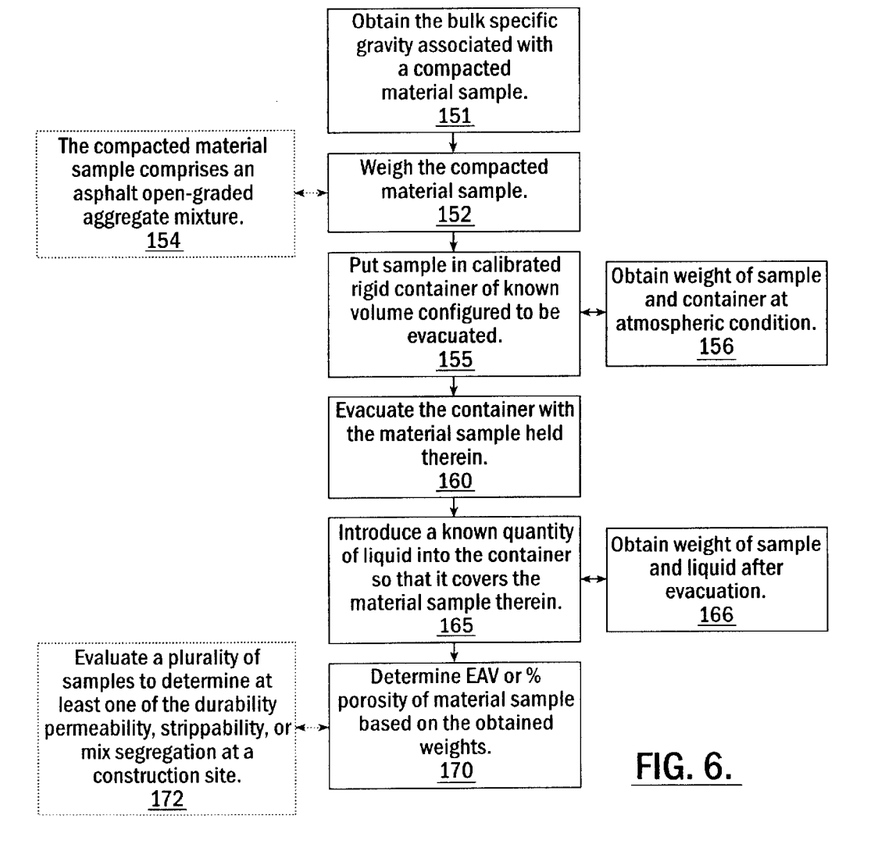
FIG. 6 is a block diagram of operations for determining effective air void content according to embodiments of the present invention.

As shown in FIG. 5, the measurement system 200 includes the container 210 which can be sealed and calibrated to obtain the empty volume. The container 210 includes a volume or level indicator means so that the level of fluid therein can be assessed. As shown, measurement indicia such as a graduated scale 211 can be positioned on a wall 210*w* of the container 210 so that the level of fluid can be visually monitored. Alternatively, a level marker can be positioned on the wall, or a plurality of level markers (which can be color coded markers) can be used to identify the appropriate level for each type or quantity of sample undergoing evaluation, if different levels are desired. In certain of the embodiments, the container is translucent or transparent so that the level can be readily observed from the outside of the container 210. Other level indicator means or monitors can alternatively or additionally be used such as, but not limited to, infrared sensors, float gauges, and the like.

The container 200 includes a vacuum port 230*p* and valve 220 in fluid communication with a vacuum source 230, and a vacuum gauge 230. The container 200 also includes a fluid inlet path 235 and outlet path 237, each operably associated with a valve 235*v*, 237*v* to control the opening and closing of the paths 235, 237. The container 210 also includes a releasable portion 250 to allow a disc or cylinder or other shape of compacted material sample 10 to be positioned in the container 200. As shown, the releasable portion 250 can be a top portion 251 which includes a fluid inlet path and outlet path port 235*p*, 237*p*, respectively. The top portion 251 can be releasably attached and sealed to the container body 210*b*. The releasable portion 250 can be attached to the container body 210*b* in any suitable manner well known to those of skill in the art. For example, the top portion 251 can be sealed and secured to the body 210*b* via a gasket, O-ring, or other sealant material and a clamping structure 260 as shown in FIG. 5. Alternatively, the releasable portion 250 can be configured to matably attach to or threadably attached to the underlying container body 210*b* (threads may be provided on the inside or outside of the top portion of the container body). In operation, the releasable portion 250 allows access to the inside of the container 210*c*. The releasable portion 250 may be otherwise formed into the container 210, such as in a sidewall or bottom portion (not shown). The valves and fluid passages can also be alternatively formed into the container 210.

The system also includes a scale 269 which can be operably associated with a computer or computer processor 275 to automatically relay and record the measured weights at particular process points as desired. Similarly, each of the valves 220, 235*v*, 237*v* can be configured to be controlled manually or by automatic controls to open and close at desired process points.

In operation, in this embodiment, the EAV, bulk density, and/or apparent maximum density of the compacted sample 10 can be calculated using the container 210 (which may be a calibrated cylinder in certain embodiments). A weight of the container or cylinder 210 can be obtained with the container in an unfilled/empty condition. Liquid or water 30 can be added to the empty cylinder 210 until it is filled to a desired level. The filled container weight can then be measured. Since the density of water is known (i.e., 1 g/cm³) and the weight of the empty cylinder is known, the amount of liquid added can also be measured to determine the container volume. For example, the container volume can be calculated by the following equation:

$$Vc = \text{Volume} = \frac{\text{Total Weight} - \text{Empty Cylinder Weight}}{\text{Density of Water}} \quad \text{Equation (2)}$$

In this embodiment, the releaseable portion 250 can be released such that a known amount of dry material sample 10 can be added to the container 210. The releaseable portion 250 (or lid) is then replaced (shown as residing on top of the cylinder) and secured or locked in position. A vacuum (with the vacuum valve 220 open) is then pulled on the container 210. The vacuum gauge 231 can be used to indicate when a proper or desired vacuum level has been established in the container 210. In certain embodiments, a vacuum level of about 29.7 inches Hg is suitable. Once the desired vacuum is achieved within the container 210, the vacuum valve 220 is closed and the water inlet valve 235*v* is opened to allow water 30 to enter into the inlet port 235*p* and into the container 210. A water level gauge 211 can be used to monitor the water level 30. As noted above, a transparent or translucent walled container can also be used to visually monitor the water level inside the container.

In any event, once the level of water 30 is above the sample 10 and reaches the level to which the empty container volume is determined, the outlet valve 237*v* can be opened to allow the water to flow out of the container 210 as desired (typically associated with methods desiring to fill the entire container volume with water). When the container 210 has the desired level of liquid or water therein, the weight of the sample plus water can be used to calculate the maximum density (apparent density) of the sample. In certain embodiments, it may be preferred to fill the container with the water to obtain the filled weight. However, other levels can also be used as long as their volumetric weights can be reliably determined/established for input/adjustment to the mathematical relationships and calculations noted below.

$$Vs = Vc - \frac{WT - WS}{WD} \quad \text{Equation (3)}$$

$$\rho_2 = \text{Apparent Density} = \frac{WS}{Vs} \quad \text{Equation (4)}$$

Where:
  Vs=volume of sample
  Vc=Calibrated or known volume of the cylinder
  WT=Weight of sample plus water in the cylinder
  WS=Weight of (dry) sample
  WD=Density of water, generally 1 g/cm³

Once the container 210 with the sample 10 has been subjected to vacuum and filled with water, the density can also be calculated by the water displacement method by submerging the entire container 210.

The process explained above can be fully automated with computer controls and appropriate sensors to monitor water level, vacuum level and valve shut off mechanism. It can also automatically monitor weights from the scale 269 and relay the measurement data to a controller 275 so that computer program products can automatically relay the weights from the scale 269 and perform the calculations and output or display the results without relying on operator input.

The invention will now be illustrated with reference to certain examples which are included herein for the purposes of illustration only, and which are not intended to be limiting of the invention.

EXAMPLES

An experiment was conducted using a 19 mm production mixture. The mix was divided into five samples consisting of a fully blended and representatively split sample, graded samples of 19 mm only, 9.5 mm, 6 mm and everything passing the #4 sieve. AASHTO T-209 test was run on each of these samples individually. The data is provided in the following table.

TABLE 1

| Sample ID | # of Tests | Sample Weight (g) | T-209 Gmm (g/cm$^3$) | % Diff From Blended Gmm |
|---|---|---|---|---|
| Fully blended sample | 5 | 1980.1 | 2.587 | — |
| Retained on 19 mm sieve (¾") | 1 | 1618.8 | 2.716 | 4.99% |
| Retained on 9.5 mm sieve (⅜") | 1 | 1650.3 | 2.620 | 1.28% |
| Retained on 6 mm sieve (#4) | 1 | 1674.2 | 2.524 | −2.44% |
| Passing #4 sieve | 1 | 1659.8 | 2.423 | −6.34% |

As is well known to those of skill in the art, the Gmm value is calculated by the following equation:

$$Gmm = w_1\rho_1 + w_2\rho_2 + w_3\rho_3 + \ldots + w_n\rho_n \qquad \text{(Equation 8)}$$

where "w" is weight fraction and "ρ" is the maximum density of each asphalt coated aggregate size within the asphalt mixture.

The above data indicates the change in the value "Gmm" due to aggregate size variation. The above data shows that Gmm can be significantly different if aggregate distribution within a sample is not uniform. Therefore, when the aggregate distribution within a compacted mixture is not uniform, one cannot simply assume that a Gmm from anther sample is representative of the compacted field core material distribution. Also, knowing that a high potential exists for aggregate distribution variation in open graded mixtures, % Air Voids might be an unreliable, or even potentially, a trivial measurement for these type of mixes.

For example, consider two randomly selected field cores from two different sections at the same job site. Assuming that the first core (Core 1) has a higher proportion of larger aggregate or rocks as compared to the second core (Core 2). With the same compactive effort, chances are that Core 1 can have more accessible voids and a higher bulk specific gravity (Gmb). Using the lab average Gmm, Core 1 will have a lower % air voids value. Core 1 can be heated and separated for determination of Gmm ("Gmm1"), the results will be relatively higher then the average Gmm and, hence, can give a higher % air voids relative to using the lab average Gmm evaluation. This core specimen or section may pass a % air voids requirements based on an average Gmm, but will have a higher air voids based on Gmm1 and, in reality, may be more prone to failure.

A problem with the conventional evaluation method in the above example case is that an increased large aggregate proportion in Core 1 creates accessible air voids that are not detected by the standardized specific density evaluation methodology (i.e., the SSD method). Also, the Gmm value based on a uniformly or relatively homogeneous split sample in the lab is not representative of the aggregate distribution of Core 1. In contrast to the % air voids method, the present invention evaluation parameter of EAV (Effective Air Voids content determination) or % porosity can indicate that Core 1 has a higher EAV value as compared to Core 2.

Thus, using the EAV calculation may allow a better prediction of the durability of the pavement over conventional testing procedures and methods. For example, using an EAV evaluation parameter in the above hypothetical situation would have indicated that the section from which Core 1 was selected would have had a higher potential of permeability and segregation. Whereas, with the conventional % air voids evaluation method, the Core 1 section may have falsely been identified as the "better" or good pavement section.

Methods for determining EAV parameter values or other properties of material specimens and characteristics according to embodiments of the present invention can be suitable for mixtures used in the preparation of concrete, asphalts, and other compacted samples.

In particular embodiments, the weight data can be directly input from the scales or from an operator into a computer for digital calculation of densities. The test methodology of the proposed methods reduce the time required to perform this test down to approximately 5–10 minutes and the use of a Rice test (evaluation of Gmm value) is not required. Advantageously, this method can be used with compacted mixtures of various compositions including coarse and/or fine aggregate mixtures as well as with high and low porosity materials.

It is expected that in particular embodiments, compacted mixtures with % porosity (EAV) values higher than about 7% may be prone to high permeability. If the pavement or the materials are designed or desired to be non-permeable, then the % porosity/EAV value may be generally targeted to be at or below about 7%. Of course, different applications and material compositions will have different target porosity goals and needs, and this estimate is not meant to be limiting to the present invention. For example, but not limited thereto, pervious concrete may have an associated target value of less than about 20% (that is, values of greater than about 20% may indicate undue permeability for certain applications).

It will be understood that each block of the flowchart illustration, and combinations of blocks in the flowchart illustrations as well as calculations, equations, data look-up charts, data manipulations, and calibration factor offset determinations, can be implemented by computer program instructions. These computer program instructions may be loaded onto a computer or other programmable data processing apparatus to produce a machine, such that the instructions which execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to allow user input (or automatic weight entry relayed by integrated scales) of data and to produce computer implemented process such that the instructions which execute on the computer or other programmable apparatus provide steps for implementing the functions specified in the flowchart block or blocks.

Accordingly, blocks of the flowchart illustrations and the numerical and mathematical relationships presented herein support combinations of means for performing the specified functions and program instruction means for performing the specified functions. It will also be understood that each block of the flowchart illustrations, and combinations of blocks in the flowchart illustrations, as well as calculations and determinations can be implemented by special purpose hardware-based computer systems which perform the specified functions or steps, or combinations of special purpose hardware and computer instructions. The blocks can be carried out in the order noted or in other orders. The operations described in the blocks can be combined or even separated into distinct operational segments. The computer systems and/or hardware can be integrated into a vacuum system or to operate with a computer associated with a vacuum system.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, when used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of determining the porosity of a compacted material sample, comprising the steps of:
   encasing a compacted material sample in a conformable sealant material;
   evacuating the encased material sample;
   sealing the encased material specimen to provide a vacuum-sealed encased material sample;
   obtaining the weight of the encased vacuum-sealed material sample in air;
   immersing the vacuum-sealed encased material sample in a liquid displacement bath;
   obtaining a weight of the encased sealed material sample with the vacuum intact while immersed in the liquid displacement bath;
   introducing an opening into the sealant material of the encased material specimen while the material specimen and sealant material are held immersed in the liquid bath to allow liquid to enter the sealant material and contact the material sample;
   obtaining the weight of the encased material sample during said immersing step after said introducing step; and
   determining the porosity of the material sample based on said obtaining steps.

2. A method according to claim 1, further comprising drying the compacted material sample, and then determining the dry weight of the material sample before said step of encasing.

3. A method according to claim 1, further comprising calculating both the density of the vacuum sealed encased compacted material sample ($\rho_1$) and the density of the vacuum sealed sample after opening the seal under liquid ($\rho_2$), and wherein said determining step comprises calculating the % porosity or effective air void content parameter value (EAV) using the mathematical equation:

$$EAV = \left(\frac{\rho 2 - \rho 1}{\rho 2}\right) \times 100.$$

4. A method according to claim 1, wherein the effective air void content parameter or % porosity is a measure of a portion of the air voids in the material sample.

5. A method according to claim 4, wherein the effective air void parameter or % porosity corresponds to air voids that are accessible to liquids during service and substantially excludes or disregards air voids in the material sample that are inaccessible to liquid during service.

6. A method according to claim 4, further comprising the step of determining the portion of inaccessible air voids in the sample.

7. A method according to claim 1, wherein the determining step determines the % porosity or the EAV of the material sample, said method further comprising:
   evaluating the material sample to determine the % air void content; and
   comparing the % air void content to the determined EAV or % porosity value.

8. A method according to claim 1, further comprising evaluating pavement durability based on the determined EAV or % porosity.

9. A method according to claim 1, wherein the sealant material is a pre-formed sealable bag having an associated apparent density, and wherein the determining step considers the apparent density of the sealant material.

10. A method according to claim 1, wherein the porosity of the compacted material sample is determined independent of an evaluation of the maximum specific gravity of the material sample.

11. A method according to claim 1, wherein the determining step determines the EAV or % porosity value, and wherein a plurality of compacted material samples are evaluated for porosity to determine their respective EAV values, the plurality of material samples being collected from different field locations at a construction site, the method further comprising monitoring variation in EAV or % porosity to identify mix segregation at the construction site.

12. A method according to claim 1, wherein the determining step determines the EAV or % porosity value, said method further comprising evaluating the potential for pavement stripping based on the determined EAV or % porosity value.

13. A method according to claim 1, wherein the determining step determines the EAV or % porosity value further comprising evaluating whether the material sample exhibits excessive permeability based on the determined EAV or % porosity.

14. A method according to claim 1, wherein the compacted material sample comprises open graded mixtures.

15. A method according to claim 1, wherein the compacted material sample is a bituminous compacted material sample.

16. A method according to claim 1, wherein the compacted material sample comprises asphalt and is obtained from a field site.

17. A method according to claim 1, wherein the compacted material sample comprises concrete.

18. A method according to claim 1, wherein the determining step determines the EAV or % porosity value of the material sample, and wherein the compacted material sample comprises an open graded mixture, the method further comprising evaluating the determined EAV or % porosity to assess the suitability of the composition of the mixture for pavement construction.

19. A method for determining the effective air void content of a compacted material sample, comprising:
   drying a compacted material sample;
   obtaining a dry weight of the material sample;
   determining the bulk specific gravity ($\rho_1$) of the material sample;
   positioning the material sample in a rigid sealable container having a known volume;
   obtaining a first weight of the material sample and container under ambient pressure conditions;
   evacuating the container to introduce a vacuum onto the material sample held therein;
   introducing a known quantity of liquid into the container in a quantity sufficient to cover the material sample;
   releasing the vacuum in the container with the material sample held immersed in the liquid;
   obtaining the weight of the material sample in the open container in the liquid after the releasing step;
   calculating the maximum apparent density ($\rho_2$); and
   determining the effective air void content or % porosity of the compacted material sample undergoing analysis based on the obtained weights, the calculated maximum apparent density ($\rho_2$) and the determined bulk specific gravity ($\rho_1$).

20. A method according to claim 19, further comprising calculating both the density of the vacuum sealed compacted material sample ($\rho_1$) and the density of the sample in the container after releasing the vacuum with the sample held under liquid ($\rho_2$) in the container, and wherein said determining step comprises calculating the effective air void content parameter value (EAV) or % porosity using the mathematical equation:

$$EAV = \left(\frac{\rho 2 - \rho 1}{\rho 2}\right) \times 100.$$

21. A method according to claim 19, wherein the effective air void content or % porosity parameter is a measure of a portion of the air voids in the material sample.

22. A method according to claim 21, wherein the effective air void or % porosity parameter corresponds to air voids that are accessible to liquids during service and substantially excludes or disregards air voids in the material sample that are inaccessible to liquid during service.

23. A method according to claim 21, further comprising evaluating the total % air void content in the material sample and then determining the percentage of inaccessible air voids in the material sample using the effective air void content or % porosity value and the % air void content value.

24. A method according to claim 19, further comprising:
   evaluating the material sample to determine the % air void content; and
   comparing the % air void content to the determined EAV or % porosity value.

25. A method according to claim 19, further comprising evaluating pavement durability based on the determined EAV or % porosity value.

26. A method according to claim 19, wherein the EAV parameter of the compacted material sample is determined independent of the determination of the maximum specific gravity of the mixture.

27. A method according to claim 19, wherein a plurality of compacted material samples are evaluated to determine their respective EAV or % porosity values, the plurality of material samples being collected from different field locations at a construction site, the method further comprising monitoring variation in EAV or % porosity to identify mix segregation at the construction site.

28. A method according to claim 19, further comprising evaluating the potential for pavement stripping based on the determined EAV or % porosity.

29. A method according to claim 19, further comprising evaluating whether the material sample exhibits excessive permeability based on the determined EAV or % porosity value.

30. A method according to claim 19, wherein the compacted material sample comprises open graded mixtures.

31. A method according to claim 19, wherein the compacted material sample is a fine graded mixture.

32. A method according to claim 19, wherein the compacted material sample is a bituminous compacted material sample.

33. A method according to claim 19, wherein the compacted material sample comprises asphalt and is obtained from a field site.

34. A method according to claim 19, wherein the compacted material sample comprises concrete.

35. A method according to claim 19, wherein the compacted material sample comprises an open graded mixture, the method further comprising evaluating the determined EAV or % porosity to assess the suitability of the composition of the mixture for asphalt pavement construction.

36. A computer program product for determining the effective air void content or % porosity of a compacted material sample undergoing analysis, the computer program product comprising:
   a computer readable storage medium having computer readable program code embodied in said medium, said computer-readable program code comprising:
      computer readable program code for accepting input corresponding to a weight measurement of a vacuum-sealed compacted material sample held encased in a sealant material;
      computer readable program code for accepting input corresponding to a weight measurement of the encased material sample as it is held under liquid with the vacuum seal intact;
      computer readable program code for accepting input corresponding to a weight measurement of the encased material sample as it is held under liquid with the vacuum seal destroyed;
      computer program code defining predetermined mathematical relationships for determining the effective air void content or % porosity of the compacted material sample; and
      computer readable program code for calculating the effective air void content or % porosity of the compacted material sample undergoing analysis based on the weight measurements and the predetermined mathematical relationships.

37. A computer program product according to claim 36, further comprising computer readable program code for calculating both the density of the vacuum sealed encased compacted material sample ($\rho_1$) and the density of the vacuum sealed sample after opening the seal under liquid ($\rho_2$), and wherein said computer readable program code for calculating air void content or % porosity comprises code that employs the mathematical equation:

$$EAV = \left(\frac{\rho 2 - \rho 1}{\rho 2}\right) \times 100.$$

38. A computer program product according to claim 36, wherein the effective air void content parameter is a measure of a subset of the air voids in the material sample.

39. A computer program product according to claim 36, wherein the effective air void parameter corresponds to air voids in the compacted material that are accessible to liquids during service and substantially excludes or disregards air voids in the compacted material sample that are inaccessible to liquid during service.

40. A computer program product according to claim 36, further comprising computer program code for evaluating the inaccessible air void content.

41. A computer program product according to claim 40, further comprising computer readable program code for evaluating the % air void content in the compacted material sample.

42. A computer program product according to claim 41, further comprising computer readable program code for comparing the % air void content value to the determined EAV or % porosity value.

43. A computer program product according to claim 36, further comprising computer readable program code for evaluating pavement durability based on the determined EAV or % porosity value.

44. A computer program product according to claim 36, wherein the material sample sealant material is a pre-formed sealable bag having an associated apparent density, and wherein the wherein the sealant material is a pre-formed sealable bag the apparent density of the sealant material when determining the EAV or % porosity value.

45. A computer program product according to claim 44, wherein the EAV or % porosity parameter of the compacted material sample excludes program code for evaluating % air void using the maximum specific gravity evaluation test.

46. A computer program product according to claim 36, further comprising computer readable program code for monitoring the EAV of a plurality of compacted material samples, the plurality of material samples being collected from different field locations at a construction site.

47. A computer program product according to claim 46, further comprising computer readable program code for evaluating variation in the monitored EAV or % porosity values over different samples obtained at a construction site to identify mix segregation at the construction site.

48. A computer program product according to claim 36, further comprising computer readable program code for evaluating the potential for pavement stripping based on the determined EAV or % porosity value.

49. A computer program product according to claim 36, further comprising computer readable program code for evaluating whether the material sample exhibits excessive permeability based on the determined EAV or % porosity value.

50. A computer program product according to claim 36, wherein the compacted material sample comprises open graded mixtures.

51. A computer program product according to claim 36, wherein the compacted material sample comprises fine graded mixtures.

52. A computer program product according to claim 36, wherein the compacted material sample is a bituminous compacted material sample.

53. A computer program product according to claim 36, wherein the compacted material sample comprises concrete.

54. A computer program product according to claim 36, wherein the compacted material sample comprises asphalt and is obtained from a field site.

55. A computer program product according to claim 36, wherein the compacted material sample comprises an open graded mixture, and wherein the computer program product further comprises computer readable program code for evaluating the determined EAV to assess the suitability of the composition of the mixture for pavement construction.

56. A system for analyzing compacted material samples, the system comprising:
   a calibrated container having a known calibrated volume configured during operation to receive a compacted material sample and a known amount of liquid;
   an evacuation source operably associated with the container;
   a weighing scale operably associated with the container; and
   computer program code for determining the effective air void content or % porosity of a compacted material sample based on an evacuated dry weight of the material sample in the container and a second wet weight of the material sample in the container after the known amount of liquid has been introduced with the vacuum released and the material sample held immersed in the liquid.

57. A system according to claim 56, wherein the weights are obtained and the effective air void content or % porosity determined in under about 10 minutes.

58. A system according to claim 56, further comprising computer program code for calculating both the density of the evacuated compacted material sample ($\rho_1$) in the container and the density of the sample under liquid ($\rho_2$) in the container, and wherein said computer readable program code for determining effective air void content comprises code for the mathematical equation:

$$EAV = \left(\frac{\rho 2 - \rho 1}{\rho 2}\right) \times 100.$$

* * * * *